United States Patent [19]

Wallroth et al.

[11] Patent Number: 4,522,213

[45] Date of Patent: Jun. 11, 1985

[54] MONITORING DEVICE FOR MEDICAL APPARATUS

[75] Inventors: Carl F. Wallroth, Lubeck; Rainer Bäuerle, Bad Schwartau, both of Fed. Rep. of Germany

[73] Assignee: Drägerwerk Aktiengesellschaft, Fed. Rep. of Germany

[21] Appl. No.: 568,112

[22] Filed: Jan. 4, 1984

[30] Foreign Application Priority Data

Jan. 25, 1983 [DE] Fed. Rep. of Germany ....... 3302321

[51] Int. Cl.$^3$ .............................................. A61B 5/08
[52] U.S. Cl. ..................................... 128/716; 128/903
[58] Field of Search ............... 128/903, DIG. 13, 716; 340/52 F

[56] References Cited

U.S. PATENT DOCUMENTS 4,227,526 10/1980 Goss ........................ 128/DIG. 13 X
4,348,653 9/1982 Tsuzuki ............................ 340/52 F

OTHER PUBLICATIONS

Botsch, F. W., Temperature, Its Measurement and Control in Science and Industry, vol. 3, Biology and Medicine, pp. 21–29.
Technical Note, "Instrumentation for a Wearable Artificial Kidney", Med. and Biol. Engrg and Comp., 1977, vol. 15, pp. 75–77.

Primary Examiner—Kyle L. Howell
Assistant Examiner—Francis J. Jaworski
Attorney, Agent, or Firm—McGlew and Tuttle

[57] ABSTRACT

In medical apparatus important parameters are monitored by special systems. In case of irregularities, signaling urging remedy occurs. The signal is to be limited to the persons monitoring the apparatus to the extent possible and should not disturb persons not involved or present in the same room, from any delicate work they may be doing. Freedom of movement of the monitoring persons is to be preserved. To accelerate corrective measures, the signal gives them information which is easy to understand about the type of disorder. For this purpose the signal transmitters for the monitored limit values are connected to a signal converter, through which a describing text in intelligible language is assigned to each signal case. These announcements are conveyed to the monitoring persons through an output means movable with them and limited to their area, such as single earphones. The earphone is connected to the signal converter through a wireless or wire-bound movable connection. Preferred application is in operating rooms or intensive care units for the monitoring of one or more equipment units or of sensors applied directly on the patient.

5 Claims, 2 Drawing Figures

MONITORING DEVICE FOR MEDICAL APPARATUS

FIELD AND BACKGROUND OF THE INVENTION

The present invention relates in general to medical equipment, and in particular to a new and useful monitoring device for for medical apparatus with pickups for at least one measured quantity and with means for signaling when given limit values are exceeded.

The health and life of patients may depend on the proper functioning of medical apparatus, as for instance respirators or anesthetizers. For this reason, monitoring devices are used for the most important functions thereof, which, when irregularities occur, give an optical or acoustic signal. The signal urges the personnel to initiate counter-measures.

A known monitoring device for respirators is equipped with a diaphragm cell connected to the gas transport lines of the respirator. A one-arm translatory lever senses the movements of the diaphragm and carries at its free end two contacts, each of which is opposite an adjustable contact screw. The contact screws are connected via lines to an alarm relay for each. During the operation of a respirator, the diaphragm cell is pressurized intermittently, so that the translatory lever executes an oscillating motion between the two contact screws. If the minimum pressure between the individual gas surges, decreases to a value below a limit value set by the contact screws, a contact is briefly closed which, via a delay unit, turns on one alarm relay after a certain number of closures of the contacts. On the other hand, if, when the maximum permissible gas pressure is exceeded, a contact between the translatory lever and the opposite contact screw is closed, the other alarm relay is turned on without delay. The two alarm relays actuate output means common to them, consisting of a buzzer and a warning light (See Swiss Pat. No. 461,711).

These output means do not address specifically the person monitoring the respirator but are perceived by all present in the vicinity. They may thus become a source of disturbance during delicate activities e.g. in the operating room. From the optical and acoustic alarm signal no clue can be derived as to which of the two limit values was exceeded, i.e. what kind of disorder is involved. Elimination of the reported disorder is thereby delayed.

In another known patient monitoring system for several persons, each of the persons to be monitored has his or her own individual monitoring unit assigned to him or her which is carried by the person, e.g. on the wrist. Several individual monitoring units cooperate with a central unit, remote-controlled by them, and having alarm signalling devices. The individual monitoring unit contains sensor means for monitoring a selected vital function, such as pulse, with production of the respective body state signal. To this end the individual monitoring unit contains signal processing means for signal processing, limit value determining means for generating an alarm signal when given limit values are exceeded, and transmitting means for relaying the alarm signal to the central unit. The relaying is done, e.g. by radio. The signal then consists of a code which indicates the emitting individual monitoring unit. The central unit contains signal receiving means, decoding means, and reporting means on which, in case of alarm, the emitting individual monitoring unit is indicated (displayed), optionally accompanied by a sound alarm (see W. German OS No. 25 35 858).

In this patient monitoring system, there is signaled to the monitoring person merely the occurrence of a limit value overstep at an identifiable monitoring point. The person is not, however, informed specifically or without disturbance to the environment. The monitoring person is tied to the location of the fixedly installed central unit and receives no specific information about the type and degree of the deviation. Also the information is limited to a single parameter.

SUMMARY OF THE INVENTION

It is the object of the present invention to provide a monitoring device for various types of medical equipment which informs the monitoring persons, without disturbance to the environment, and also when the monitoring persons are away from the monitored apparatus, about the presence of a signal and its identification, in an easily intelligible manner.

Accordingly, an object of the invention is to provide a device for monitoring at least one parameter sensed by a medical unit which determines when the parameter has exceeded or fallen below set limit values and produces an audible, intelligible language signal stating the parameter which is at an abnormal level, and whether the level is too high or low.

The advantages achieved with the invention consist in particular, in that the conversion of the signals of the signal transmitters into different texts correlated with the various disorders in intelligible language, not only the presence but also the type of disorder becomes readily comprehensible to the monitoring persons, in a generally understandable manner. The taking of countermeasures is thereby accelerated. Owing to the simple identification, for the monitoring of several measured quantities, output via one output means for each monitoring person monitored is sufficient. This is very helpful if the environment should not be disturbed by the signal. At the same time, the simple identification offers great freedom in use, in that several parameters within an equipment to be monitored or parameters from different equipment or from sensors directly applied on the patient, can be monitored singly or jointly. The giving out of the spoken text via movable means makes it possible for the monitoring person to carry the device, who thus can stay at different distances from the monitoring equipment. Due to the short range of the output, the signals are understandable only to the monitoring person, without disturbing the environment.

A further object of the invention is to provide such a monitoring device wherein the audible text or language information is provided from a signal converter to an audio output such as an earphone, by a cable or by a transmitter/receiver combination.

Here the connection in the form of a cable makes possible an especially economical mobility over small distances, while a wireless connection permits increased mobility. An earphone is a preferred means of individual voice output, while the arrangement on one side only leaves intact the perceptibility of noises from the environment.

According to another feature of the invention, tactile elements are connected after the signal transmitters. They may be of advantage wherever the monitoring person is disturbed by surrounding noises.

Another object of the invention is to provide a method of monitoring at least one parameter produced by medical equipment, which produces an audible, intelligible language or text signal indicating the parameter involved, and whether the value for the parameter is too high or too low.

A further object of the invention is to provide a monitoring device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
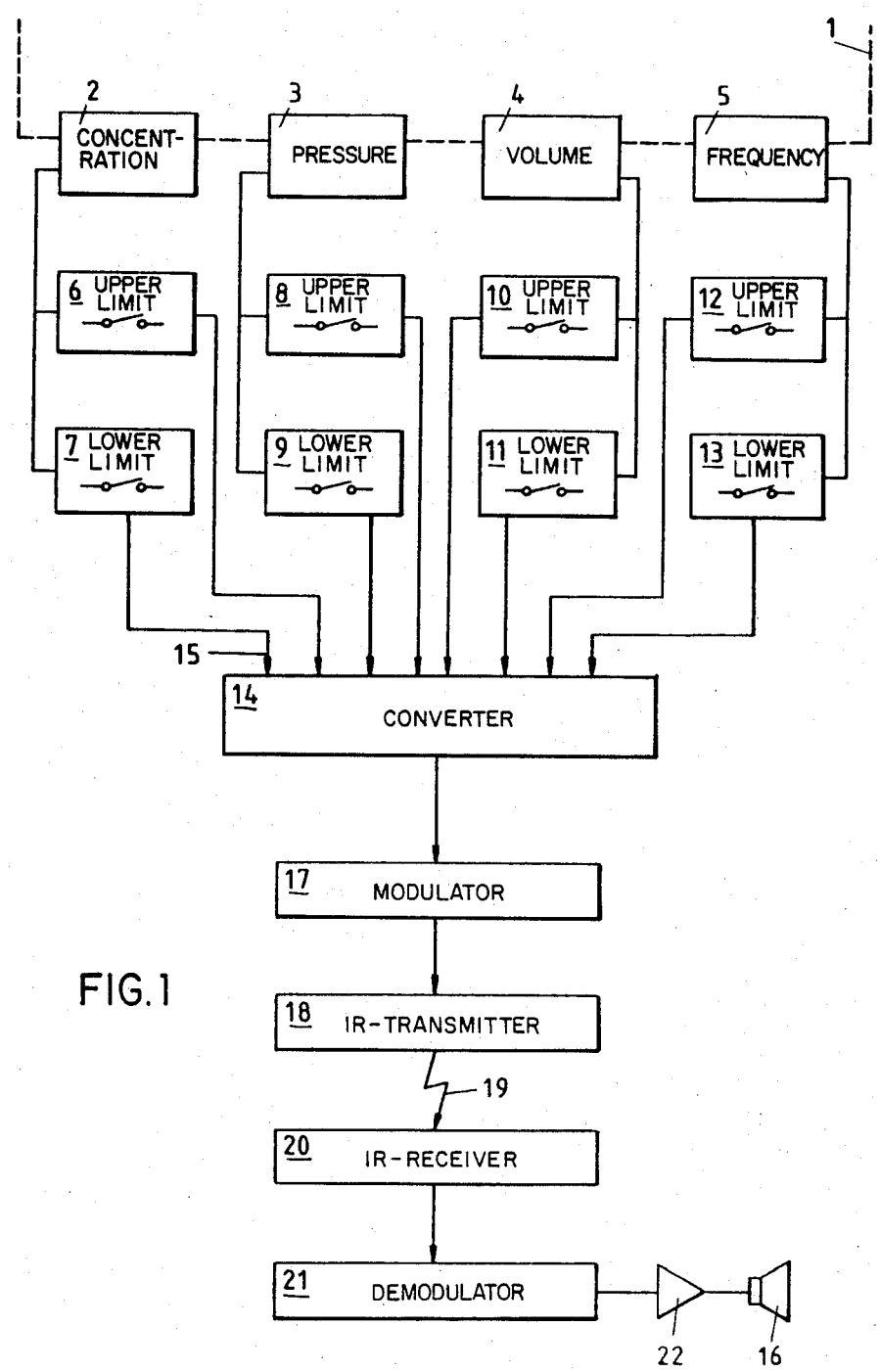
FIG. 1 is a block diagram of a monitoring device with one output means.
Figure 2:
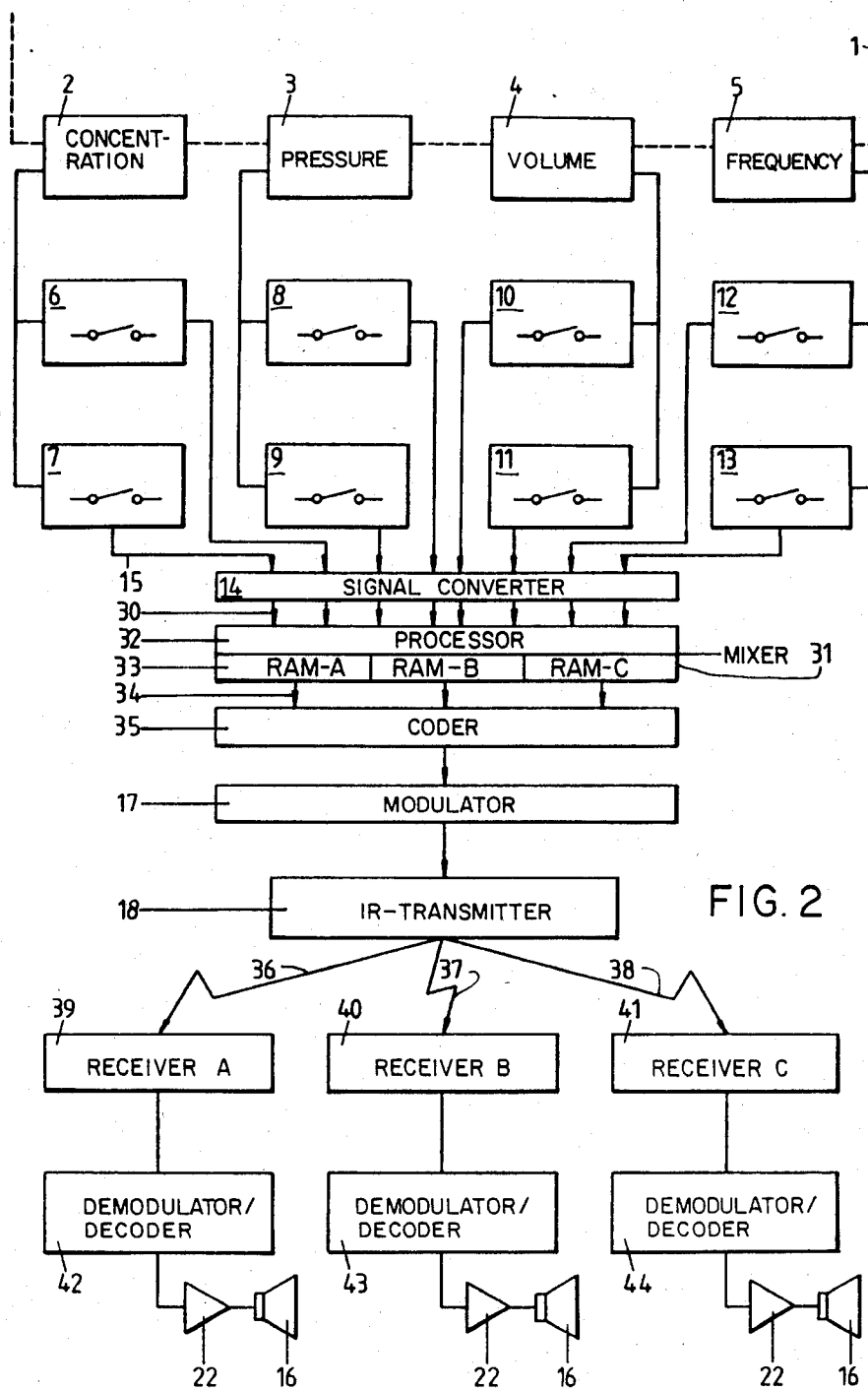
FIG. 2 is a block diagram of a monitoring device with several output means.

Referring to the drawings in particular, the invention embodied therein comprises a monitoring device which can be used in conjunction with medical apparatus or equipment, designated 1 in FIGS. 1 and 2. This equipment can be for example, a respirator for providing air to a patient, or for providing air and anesthesia to the patient. Such respirators are known to include sensors for sensing concentrations, for example of oxygen or anesthetic, pressure at various points during the breathing cycle, volume of air being inhaled and exhaled by the patient, and the frequency of the inhaling and exhaling cycles.

At suitable measuring points, such as in air lines or at setting devices such as valves, sensors 2 to 5 for the parameters to be monitored, such as concentration, pressure, volume and frequency, are arranged. The output signal of each sensor 2 to 5 controls one pair each of signal transmitters 6 to 13, one of which (6,8,10 and 12) is set to the upper limit value to be monitored, while the other of which (7,9,11 and 13) is set to the lower limit value. Each output of a signal transmitter 6 to 13 is connected to a separate input of a signal converter 14.

In the embodiment of FIG. 1, the signal converter 14 delivers for the signal arriving at its various inputs 15, different frequency sequences of synthetic language assigned to the respective input, the content of which relates to the connected sensor (e.g. sensor 2 for concentration) and to signal transmitters (e.g. signal transmitter 7 for the lower limit value). The relaying of the voice signal to the output means 16, a one-sided earphone worn by the monitoring person, occurs via a modulator 17 which controls an infrared transmitter 18. The radiation of transmitter 18, over the transmission distance 19, is absorbed by an infrared receiver 20 and supplied to the output means 16 via a demodulator 21 and an amplifier 22. The parts, infrared receiver 20, demodulator 21 and amplifier 22, together with a current supply, are assembled with the earphone of the output means 16 and are freely portable.

In the embodiment of FIG. 2, where similar elements have similar members, the signal converter 14 sends, for each signal arriving at the various inputs 15, on a respective voice line 30 a corresponding voice signal into a mixer 31. There, in a processor 32, according to a program, they are allocated to one or more memories (RAM's) 33, the signals of which are then available there at the following output means 16 to the respective specialized personnel, e.g. physician, nurse and technician, already decoded according to area of interest.

To this end, a coder 35 recalls successively via memory lines 34 the content of each memory 33 and then sends the data blocks via the modulator 17 to the transmitter 18. Thence they are transmitted via the transmission distances 36, 37 and 38 to all receivers, e.g. A at 39 for the physician, B at 40 for the nurse, and C at 41 for the technician, and are supplied via demodulator/decoder 42 to 44 and amplifiers 22 to the output means 16 for the physician, nurse or technician.

The IR transmitter 18 as well as the IR receivers 20, 39, 40 and 41, are of known designs. Any transmitter/receiver combination can be utilized as well, such as a radio frequency transmitter and receiver. The lines 19, 36, 37 and 38 may also signify cables connecting the transmitting part of the monitor to the receiving part of the monitor, in accordance with the invention.

In both embodiments, sufficient prerecorded information is present in the signal converter 14 for producing the various audible texts or phrases.

For example, if the signal from sensor 2 indicates that the concentration of anesthesia is too high, upper limit unit 6 will be activated sending a signal over its connecting line to signal converter 14. Each connecting line functions to engage a particular language signal, which can for example be stored on a separate track on a magnetic tape. With unit 6 activated, the audible signal may be "anesthesia concentration high". This audible signal is sent to the modulator 17 for making it acceptable by the transmitter 18, which transmits the signal to the receiver 20. Demodulator 21 converts the transmitted signal back to a signal which can be amplified and provided to earphone 16 so that it can be heard by the monitoring person wearing the earphone 16.

Other sound tracks in signal converter 14 may, for example, be "respiratory pressure low", "inhalation volume high" or "respiration frequency low".

The other elements shown in FIGS. 1 and 2 are also all known in the art so that the invention can be assembled of conventional parts.

While specific embodiments of the invention have been shown and described in detail to illustrate the application of the principles of the invention, it will be understood that the invention may be embodied otherwise without departing from such principles.

What is claimed is:

1. In a monitoring device for a respirator which is capable of generating a plurality of parameter level signals corresponding to physiological quantities for a patient, said physiological quantities including the concentration of oxygen in respiratory gas for the patient, a concentration of anesthesia for respiratory gas of the patient, the pressure of respiratory gas for the patient, the volume of respiratory gas for the patient and the frequency of respiration for the patient, the circuitry comprising:

separate low limit value transmitter means for receiving each parameter level signal and for generating a low level signal when the parameter level signal is below a selected limit value for the parameter level signal;

separate high limit value transmitter means for receiving each parameter level signal and for generating a high limit signal when the parameter level signal is above a selected limit value for the parameter level signal;

signal converter means for converting each low and high limit signal into a separate intelligible language level signal indicating the type of physiological quantity which corresponds to the parameter level, and the fact that the parameter level is outside its selected limit value;

modulator means connected to said signal converter means for converting each intelligible language signal into a modulated signal;

wireless transmitter means connected to said modulator means for transmitting each modulated signal across a distance;

a plurality of wireless receiver means each for receiving at least one modulated signal from said wireless transmitter means over said distance and each adapted to be worn by a medical person attending for the patient;

demodulator means connected to each receiver means for demodulating said modulated signal into said intelligible language signal;

amplifier means connected to each demodulator means for amplifying said intelligible language signal; and earphone means connected to each amplifier means for producing audible intelligible language and adapted to be worn by the medical person.

2. A monitoring device according to claim 1, wherein said wireless transmitter means and said wireless receiver means comprise an infrared transmitter and receiver respectively.

3. A monitoring device according to claim 1, including signal mixing means connected to said signal converter means for receiving a plurality of intelligible language signals, a plurality of memory units connected to said signal mixing means for separating the plurality of parameter level signals into a plurality of groups of signals, one group for each memory unit, a coding means connected to said plurality of memory units for encoding each intelligible language signal with an indication of which group the parameter level signal corresponding to an intelligible language signal corresponds, said modulator means connected to said coding means for modulating the encoded intelligible language signals, one receiver means being associated with said transmitter means for each group, each receiver means being capable of receiving the encoded intelligible language signal for its group, decoder means connected to each receiver means for decoding the modulated signal to produce the intelligible language signal.

4. A method for medical personnel to monitor a plurality of parameter levels corrsponding to physiological quantities supplied to a patient by a respirator including the concentration of oxygen and respiratory gas, the concentration of anesthesia in the respiratory gas, the pressure and volume of the respiratory gas and the frequency of breathing for the patient, comprising:

generating a low limit value signal when a parameter level signal falls below a selected limit value for the parameter level signal;

generating a high limit value signal when a parameter level signal rises above the selected limit value for the parameter level signal;

converting each high and each low limit value signal to an intelligible language signal which indicates the fact that the parameter level signal has gone outside the selected limit value and which physiological quantity the parameter level signal corresponds to;

modulating the intelligible language signal;

transmitting the modulated intelligible language signal to a location spaced from the patient;

receiving the transmitted modulated intelligible language signal at the spaced location;

demodulating the received intelligible language signal to produce an audible language signal; and providing the audible language signal over an earphone to be worn by a medical person for the patient.

5. A method according to claim 4 including dividing the physiological quantities into areas of interest for a plurality of medical people and transmitting only those physiological quantities to those people whose interest the physiological quantities fall into.

* * * * *